US009846483B2

(12) United States Patent
Petrov

(10) Patent No.: US 9,846,483 B2
(45) Date of Patent: Dec. 19, 2017

(54) HEADSET WITH CONTACTLESS ELECTRIC FIELD SENSORS FOR FACIAL EXPRESSION AND COGNITIVE STATE DETECTION

(71) Applicant: Oculus VR, LLC, Menlo Park, CA (US)

(72) Inventor: Yury Anatolievich Petrov, Coto de Caza, CA (US)

(73) Assignee: Oculus VR, LLC, Menlo Park, CA (US)

( * ) Notice: Subject to any disclaimer, the term of this patent is extended or adjusted under 35 U.S.C. 154(b) by 28 days.

(21) Appl. No.: 14/970,301

(22) Filed: Dec. 15, 2015

(65) Prior Publication Data
US 2017/0168568 A1    Jun. 15, 2017

(51) Int. Cl.
*G06F 3/01* (2006.01)
*A61B 5/0476* (2006.01)
*A61B 5/16* (2006.01)
*G02B 27/01* (2006.01)

(52) U.S. Cl.
CPC ............ *G06F 3/015* (2013.01); *A61B 5/0476* (2013.01); *A61B 5/16* (2013.01); *G02B 27/01* (2013.01)

(58) Field of Classification Search
CPC ......... G06F 3/015; A61B 5/0476; A61B 5/16; G06T 13/40; G06T 19/006
USPC ............................................................. 345/8
See application file for complete search history.

(56) References Cited

U.S. PATENT DOCUMENTS

| 5,583,795 | A  | * | 12/1996 | Smyth ................. A61B 3/0025 359/630 |
| 8,605,008 | B1 | * | 12/2013 | Prest .................. G02B 27/0176 345/7 |
| 2011/0234489 | A1 | * | 9/2011 | Van Acht ................. A61B 5/11 345/156 |
| 2013/0208234 | A1 | * | 8/2013 | Lewis ..................... G06F 3/011 351/158 |
| 2016/0077547 | A1 | * | 3/2016 | Aimone .................. G06F 3/012 345/8 |

OTHER PUBLICATIONS

Yury Petrov and Srinivas Sridhar, "Electric Field Encephalography as a Tool for Functional Brain Research: A Modeling Study," Jul. 3, 2013.*

* cited by examiner

Primary Examiner — Stephen Sherman
(74) Attorney, Agent, or Firm — Fenwick & West LLP

(57) ABSTRACT

A head-mounted display (HMD) device includes a plurality of activity detection sensors coupled to a liner formed around a periphery of a HMD or a band attached to the HMD. The sensors attached to the liner are adopted for direct or indirect contact to an upper portion of a user's face, and the sensors coupled to the band are adopted for direct or indirect contact with a back side of the user's head. The activity detection sensors detect electrical field signals caused by muscle contractions in an upper portion of a user's face or brain activity signals when the user is wearing the HMD. The HMD includes a module that reconstructs and projects a facial animation model of the user and a cognitive state of the user based on signals from the activity detection sensors while the HMD is in use by the user.

12 Claims, 4 Drawing Sheets

HEADSET WITH CONTACTLESS ELECTRIC FIELD SENSORS FOR FACIAL EXPRESSION AND COGNITIVE STATE DETECTION

BACKGROUND

The present invention generally relates to the field of capturing facial expressions and cognitive states of users wearing a head-mounted display (HMD).

The recent introduction of consumer-level HMDs has led to a revival in virtual reality and is drawing wide interest from consumers for gaming and online virtual worlds. With the help of existing motion capture and hand tracking technologies, users can navigate and perform actions in fully immersive virtual environments. But users lack a technological solution for face-to-face communication that conveys compelling facial expressions in virtual environments.

Facial animation has been mostly dominated by optical capture systems that use cameras or depth sensors. Methods for facial representations, tracking, mapping, and animation have been developed, greatly impacting film and game production. However, because a typical face is more than 60% occluded by a HMD, established optical sensing methods that achieve the desired facial tracking quality fail to capture nearly the entire upper face. Also, typical uses of HMD in virtual reality involve head and body rotations and large amplitude movements, making it difficult to capture facial expressions by a stationary camera or a set of stationary cameras.

There also lacks a technological solution for effective cognitive and emotional state monitoring of the user of the HMD, which can be beneficial to the user for both health purposes and enhancing the immersiveness of the virtual reality experience. For example, monitoring the user's fatigue while a user is playing a game in the virtual reality environment could prevent excessive use of the HMD that may be harmful to the user.

SUMMARY

Embodiments of the invention use a plurality of activity detection sensors in direct or indirect contact with various different locations on an upper portion of a user's face and a back side of the user's head. For example, the HMD includes a liner formed around a periphery of the HMD, and a band attached to the HMD that fastens the HMD to the user's head. The activity detection sensors are attached along various locations of the liner and the band, and are configured to measure electrical signals caused, for example, by muscle contractions of the user's upper face and brain activity waves of the user when the user is wearing the HMD. Each signal detected by an activity detection sensor is a mixture of individual source signals. In one embodiment, the activity detection sensors are electrical field sensors that detect electrical field signals from muscle contractions and the brain.

The HMD includes a module that identifies a set of individual source signals that constitute the received signals from the plurality of activity detection sensors. The module uses the set of source signals to project a facial animation model of the user's face onto the virtual reality environment while the HMD is in use by the user. The module also uses the set of source signals to display the cognitive state of the user onto the virtual reality environment while the HMD is in use by the user.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

Overview

Figure 1:
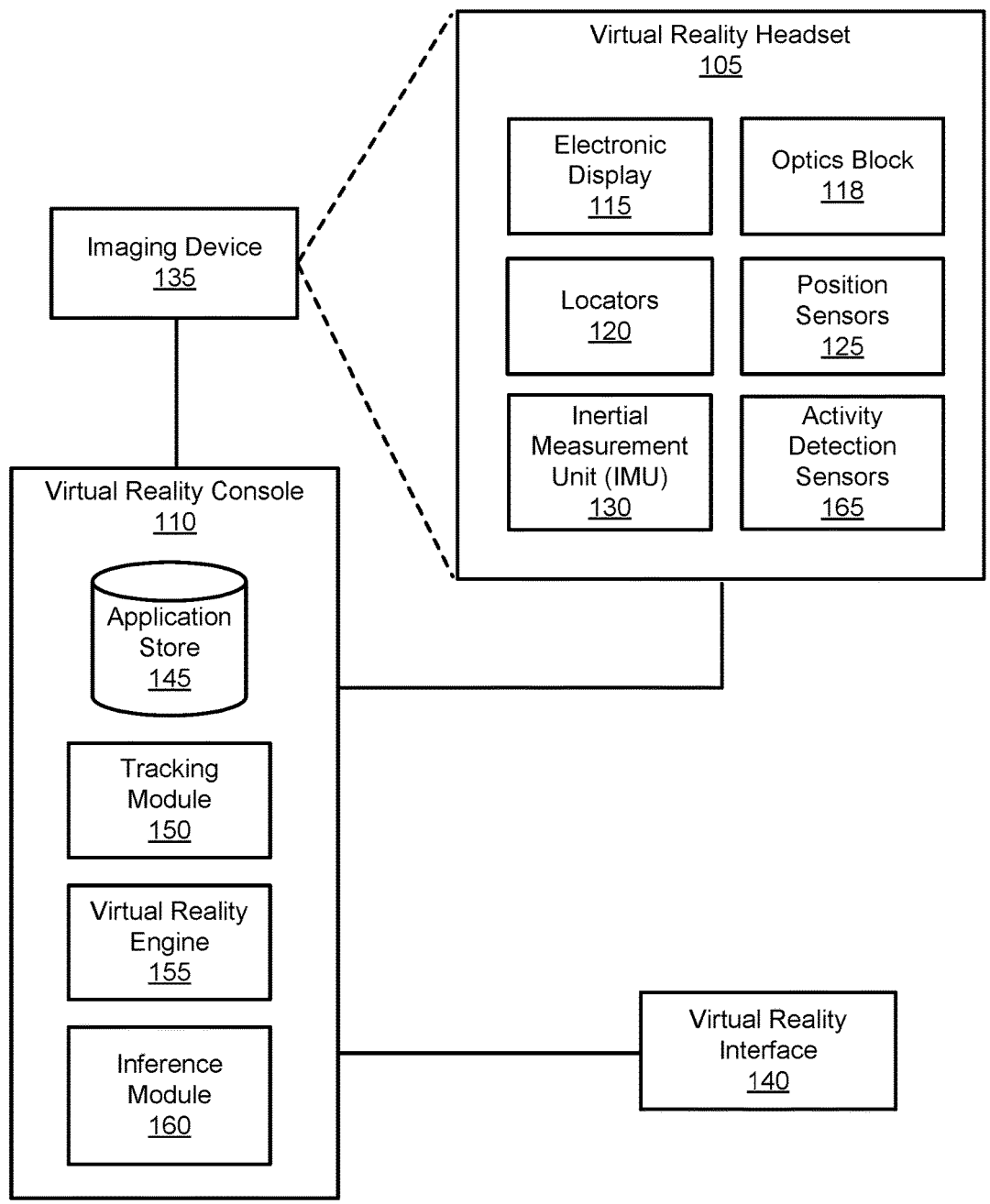
FIG. 1 is a block diagram of a system environment including a virtual reality system, in accordance with an embodiment.

FIG. 1 is a block diagram of a virtual reality (VR) system environment 100 in which a VR console 110 operates. The system environment 100 shown by FIG. 1 comprises a VR headset 105, an imaging device 135, and a VR input interface 140 that are each coupled to the VR console 110. While FIG. 1 shows an example system 100 including one VR headset 105, one imaging device 135, and one VR input interface 140, in other embodiments any number of these components may be included in the system 100. For example, there may be multiple VR headsets 105 each having an associated VR input interface 140 and being monitored by one or more imaging devices 135, with each VR headset 105, VR input interface 140, and imaging devices 135 communicating with the VR console 110. In alternative configurations, different and/or additional components may be included in the system environment 100.

The VR headset 105 is a head-mounted display (HMD) that presents media to a user. Examples of media presented by the VR head set include one or more images, video, audio, or some combination thereof. An embodiment of the VR headset 105 is further described below in conjunction with FIG. 2. The VR headset 105 may comprise one or more rigid bodies, which may be rigidly or non-rigidly coupled to each other together. A rigid coupling between rigid bodies causes the coupled rigid bodies to act as a single rigid entity. In contrast, a non-rigid coupling between rigid bodies allows the rigid bodies to move relative to each other.

The VR headset 105 includes an optics block 118, one or more locators 120, one or more position sensors 125, an inertial measurement unit (IMU) 130, and a plurality of activity detection sensors 165.

The electronic display 115 displays images to the user in accordance with data received from the VR console 110.

The optics block 118 magnifies received light, corrects optical errors associated with the image light, and presents the corrected image light to a user of the VR headset 105. In various embodiments, the optics block 118 includes one or more optical elements. Example optical elements included in the optics block 118 include: an aperture, a Fresnel lens, a convex lens, a concave lens, a filter, or any other suitable optical element that affects image light. Moreover, the optics block 118 may include combinations of different optical elements. In some embodiments, one or more of the optical elements in the optics block 118 may have one or more coatings, such as anti-reflective coatings.

The locators 120 are objects located in specific positions on the VR headset 105 relative to one another and relative to a specific reference point on the VR headset 105. A locator 120 may be a light emitting diode (LED), a corner cube reflector, a reflective marker, a type of light source that contrasts with an environment in which the VR headset 105 operates, or some combination thereof. In embodiments where the locators 120 are active (i.e., an LED or other type of light emitting device), the locators 120 may emit light in the visible band (~380 nm to 750 nm), in the infrared (IR) band (~750 nm to 1 mm), in the ultraviolet band (10 nm to 380 nm), in some other portion of the electromagnetic spectrum, or in some combination thereof.

The IMU 130 is an electronic to an initial position of the VR headset 105 based on measurement signals received from device that generates fast calibration data indicating an estimated position of the VR headset 105 relative one or more of the position sensors 125. A position sensor 125 generates one or more measurement signals in response to motion of the VR headset 105. Examples of position sensors 125 include: one or more accelerometers, one or more gyroscopes, one or more magnetometers, another suitable type of sensor that detects motion, a type of sensor used for error correction of the IMU 130, or some combination thereof. The position sensors 125 may be located external to the IMU 130, internal to the IMU 130, or some combination thereof.

The plurality of activity detection sensors 165 capture facial movement of a user's upper face and brain activity of the user. The facial movement signals detected by the plurality of activity detection sensors 165 can be used to project an animated version of the user's face onto the virtual reality environment. The brain activity signals detected by the plurality of activity detection sensors 165 can be used to infer the emotional or cognitive state, such as degree of concentration, fatigue, and relaxation, of the user. The plurality of activity detection sensors 165 are attached along a periphery of the VR headset 105, and along a band of the VR headset 105 that fastens the VR headset 105 to the user's head. An embodiment of the plurality of activity detection sensors 165 is further described below in conjunction with FIGS. 2 and 3.

In one particular embodiment referred to throughout the remainder of the application, each of the plurality of activity detection sensors 165 are electric field sensors that capture facial movement signals in the form of electric field signals generated by muscle contractions of the user's upper face, and brain activity signals in the form of electric fields generated by brain waves of the user. It is appreciated, however, that in other embodiments of the activity detection sensors 165 are alternatively and/or additionally include other sensors, such as capacitive sensors, inductive sensors, electroencephalogram (EEG) sensors, or magnetoencephalogram (MEG) sensors that capture muscle movement or brain activity of the user as electrical or magnetic signals.

The imaging device 135 generates slow calibration data in accordance with calibration parameters received from the VR console 110. Slow calibration data includes one or more images showing observed positions of the locators 120 that are detectable by the imaging device 135. The imaging device 135 may include one or more cameras, one or more video cameras, any other device capable of capturing images including one or more of the locators 120, or some combination thereof. Additionally, the imaging device 135 may include one or more filters (e.g., for increasing signal to noise ratio). The imaging device 135 is configured to detect light emitted or reflected from locators 120 in a field of view of the imaging device 135. In embodiments where the locators 120 include passive elements (e.g., a retroreflector), the imaging device 135 may include a light source that illuminates some or all of the locators 120, which retroreflect the light towards the light source in the imaging device 135. Slow calibration data is communicated from the imaging device 135 to the VR console 110, and the imaging device 135 receives one or more calibration parameters from the VR console 110 to adjust one or more imaging parameters (e.g., focal length, focus, frame rate, ISO, sensor temperature, shutter speed, aperture, etc.).

The VR input interface 140 is a device that allows a user to send action requests to the VR console 110. An action request is a request to perform a particular action. For example, an action request may be to start or to end an application or to perform a particular action within the application. The VR input interface 140 may include one or more input devices. Example input devices include a keyboard, a mouse, a game controller, a joystick, a yoke, or any other suitable device for receiving action requests and communicating the received action requests to the VR console 110. An action request received by the VR input interface 140 is communicated to the VR console 110, which performs an action corresponding to the action request. In some embodiments, the VR input interface 140 may provide haptic feedback to the user in accordance with instructions received from the VR console 110. For example, haptic feedback is provided when an action request is received, or the VR console 110 communicates instructions to the VR input interface 140 causing the VR input interface 140 to generate haptic feedback when the VR console 110 performs an action.

The VR console 110 provides content to the VR headset 105 for presentation to the user in accordance with information received from one or more of: the imaging device 135, the VR headset 105, and the VR input interface 140. In the example shown in FIG. 1, the VR console 110 includes an application store 145, a tracking module 150, a virtual reality (VR) engine 155, and an inference module 160. Some embodiments of the VR console 110 have different components than those described in conjunction with FIG. 1. Similarly, the functions further described below may be distributed among components of the VR console 110 in a different manner than is described here.

The application store 145 stores one or more applications for execution by the VR console 110. An application is a group of instructions, that when executed by a processor, generates content for presentation to the user. Content generated by an application may be in response to inputs received from the user via movement of the VR headset 105 or the VR interface device 140. Examples of applications include gaming applications, conferencing applications, video playback application, or other suitable applications.

The tracking module 150 calibrates the system environment 100 using one or more calibration parameters and may adjust one or more calibration parameters to reduce error in determination of the position of the VR headset 105. For example, the tracking module 150 adjusts the focus of the imaging device 135 to obtain a more accurate position for observed locators on the VR headset 105. Moreover, calibration performed by the tracking module 150 also accounts for information received from the IMU 130. Additionally, if tracking of the VR headset 105 is lost (e.g., the imaging device 135 loses line of sight of at least a threshold number of the locators 120), the tracking module 140 re-calibrates some or all of the system environment 100.

The VR engine 155 executes applications within the system environment 100 and receives position information, acceleration information, velocity information, predicted future positions, or some combination thereof, of the VR headset 105 from the tracking module 150. Based on the received information, the VR engine 155 determines content to provide to the VR headset 105 for presentation to the user. For example, if the received information indicates that the user has looked to the left, the VR engine 155 generates content for the VR headset 105 that mirrors the user's movement in a virtual environment. Additionally, the VR engine 155 performs an action within an application executing on the VR console 110 in response to an action request received from the VR input interface 140 and provides feedback to the user that the action was performed. The provided feedback may be visual or audible feedback via the VR headset 105 or haptic feedback via the VR input interface 140.

The inference module 160 receives and processes signals from the plurality of activity detection sensors 165, and projects an animated version of the user's face and the user's cognitive state onto the virtual reality environment while the VR headset 105 is in use. For example, the inference module 160 may determine that the user is smiling and project an animated smiling face onto the virtual reality environment. As another example, the inference module 160 may display how fatigue the user is so the user can discontinue using the VR headset 105, and prevent excessive use of the VR headset 105. An embodiment of the inference module 160 is described below in further detail in conjunction with FIG. 5.

Virtual Reality Headset

Figure 2:
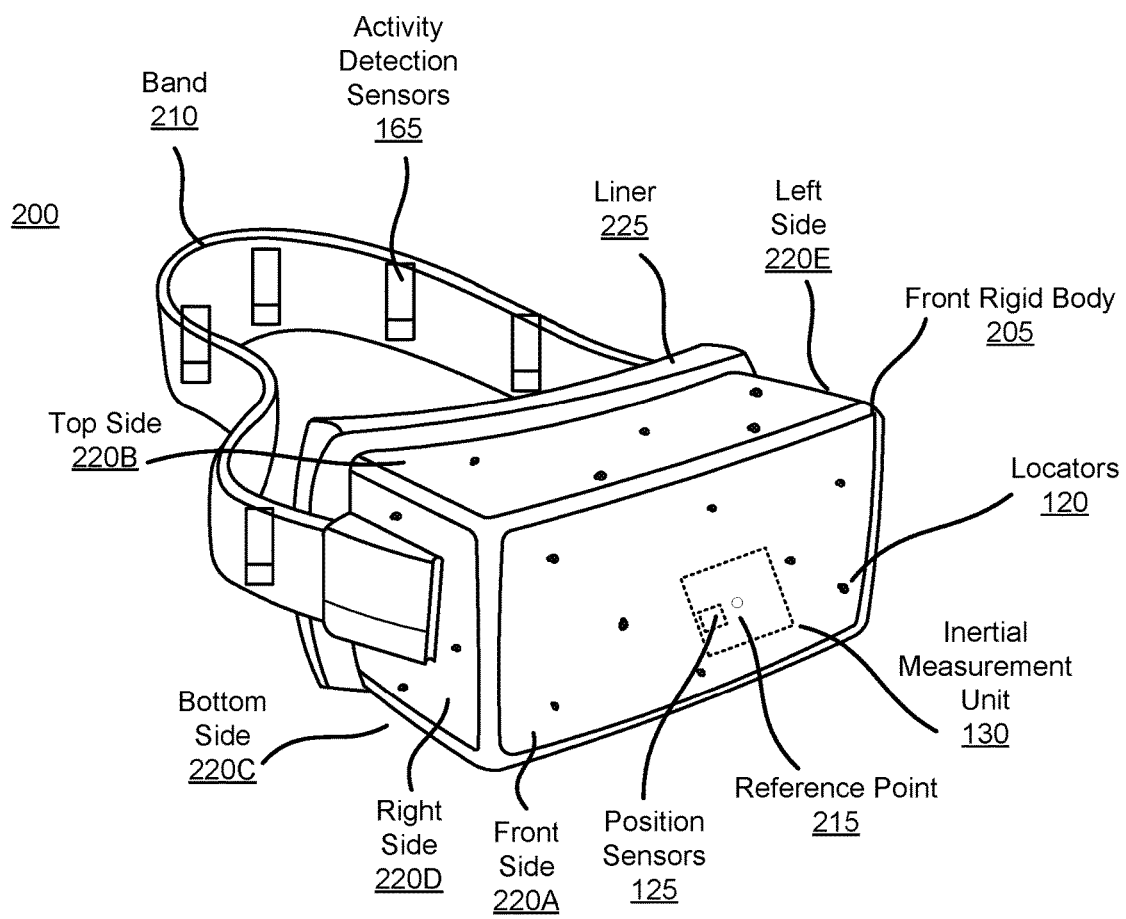
FIG. 2 is a wire diagram of a virtual reality headset, in accordance with an embodiment.

FIG. 2 is a wire diagram of a virtual reality (VR) headset 200, in accordance with an embodiment. The VR headset 200 is an embodiment of the VR headset 105, and includes a front rigid body 205 and a band 210. The front rigid body 205 includes one or more electronic display elements of the electronic display 115 (not shown), the IMU 130, the one or more position sensors 125, the locators 120, and a liner 225 around the periphery of the front rigid body 205. In the embodiment shown by FIG. 2, the position sensors 125 are located within the IMU 130, and neither the IMU 130 nor the position sensors 125 are visible to the user.

The locators 120 are located in fixed positions on the front rigid body 205 relative to one another and relative to a reference point 215. In the example of FIG. 2, the reference point 215 is located at the center of the IMU 130. Each of the locators 120 emit light that is detectable by the imaging device 135. Locators 120, or portions of locators 120, are located on a front side 220A, a top side 220B, a bottom side 220C, a right side 220D, and a left side 220E of the front rigid body 205 in the example of FIG. 2.

Figure 3:
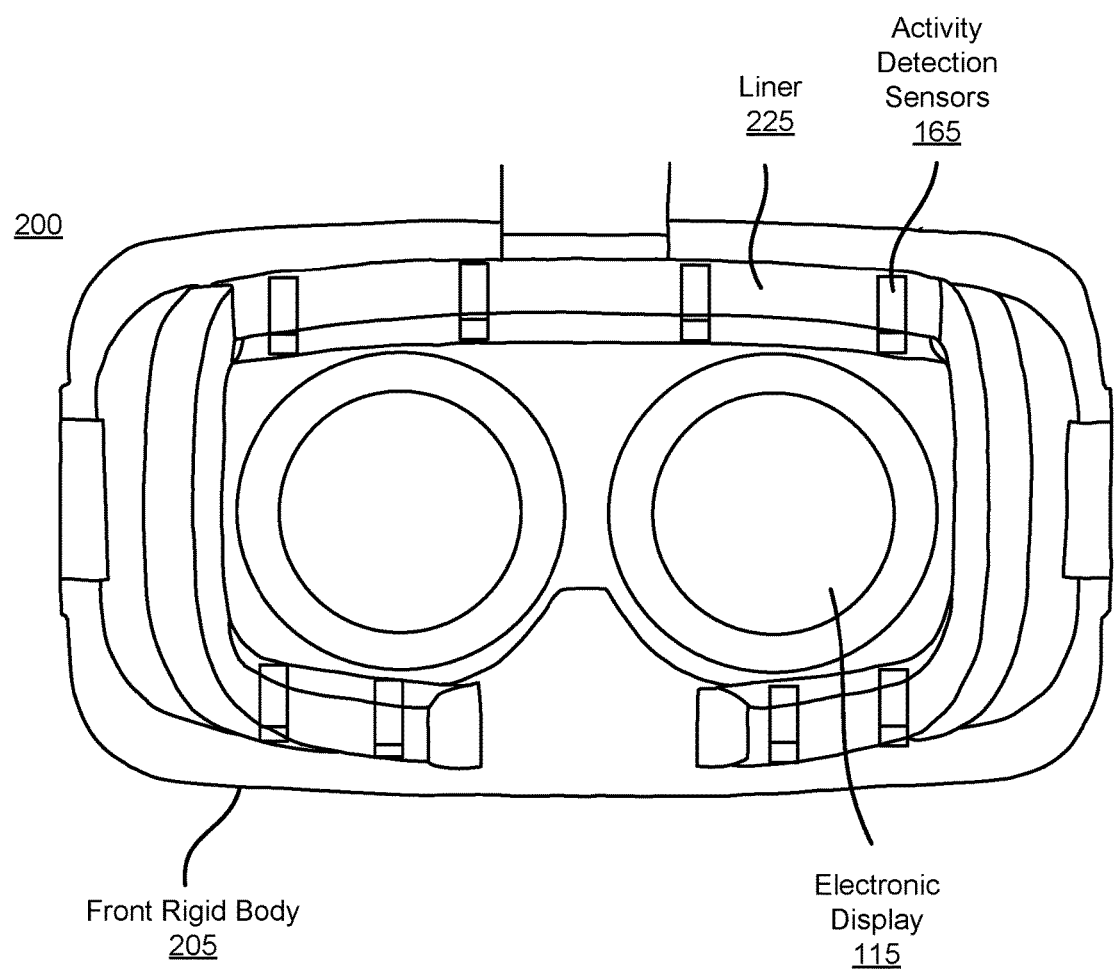
FIG. 3 is a wire diagram of an embodiment of the front rigid body of the VR headset shown in FIG. 2 having a plurality of activity detection sensors, in accordance with an embodiment.

FIG. 3 is a wire diagram of an embodiment of the front rigid body 205 of the VR headset shown in FIG. 2 having a plurality of activity detection sensors 165, in accordance with an embodiment.

The front rigid body 205 includes a liner 225 and a plurality of activity detection sensors 165 along a plurality of locations of the liner 225. The plurality of activity detection sensors 165 along the liner 225 may be used to detect both facial movement signals and brain activity signals of the user. The liner 225 is formed around a periphery of the front rigid body 205 of the VR headset 200. The liner 225 is adapted for direct or indirect contact with an upper portion of a user's face. In one embodiment, the plurality of sensors 165 may be positioned underneath the liner 225 or underneath a padding of the liner 225 so the activity detection sensors 165 do not directly contact the user's upper face. In another embodiment, the plurality of activity detection sensors 165 may be securely attached along a plurality of locations along the liner 225, in indirect or direct contact with the user's upper face.

Returning to FIG. 2, the VR headset 200 may also include a plurality of activity detection sensors 165 along a plurality of locations of the band 210. The plurality of activity detection sensors 165 along the band 210 may primarily be used to detect brain activity signals of the user generated from the back side of the user's head. In one embodiment, the plurality of activity detection sensors 165 may be positioned underneath a padding of the band 210 so the activity detection sensors 165 do not directly contact the back side of the user's head. In another embodiment, the plurality of activity detection sensors 165 may be securely attached along a plurality of locations along the band 210, in indirect or direct contact with a back side of the user's head when the headset 200 is worn by the user. In another embodiment, at least a portion of the plurality of activity detection sensors 165 may be attached to the band 210 in a position corresponding to the parietal lobe and the temporal lobe of the user to effectively detect brain activity signals of the user.

The plurality of activity detection sensors 165 may be configured to detect electric field signals typically generated by muscle contractions in the user's upper face, which may be approximately 100 mV/m and within the frequency range of 7-20 Hz. The plurality of sensors 165 may also be configured to detect electric field signals typically generated by brain waves of the user, which may be in the frequency range of 8-25 Hz. For example, the plurality of activity detection sensors 165 may be configured to detect alpha brain waves (frequency range 8-12 Hz), beta brain waves (frequency range 17-25 Hz) of the user, or both.

In one embodiment, a portion of the plurality of activity detection sensors 165 may have a higher sensitivity of detecting electrical or magnetic signals than the remaining portion of the plurality of activity detection sensors 165. For example, since electrical field signals from brain activity are approximately 10-100 times weaker than electric field signals from muscle contractions, a portion of the plurality of activity detection sensors 165 may have higher sensitivity for capturing brain activity signals with weaker intensity.

A signal detected by an activity detection sensor 165 is a mixture of signals from distinct individual sources, and may include both facial movement signals and brain activity signals of the user. The individual sources may be muscles at different locations around the user's face or various brain wave signals from different locations of the user's brain. For example, although muscle contractions produce strong electric fields localized around individual muscles, an activity detection sensor 165 at a location corresponding to an individual muscle may contain other signals in addition to the electric field generated by the individual muscle. The additional signals may be electric fields generated from contractions of neighboring muscles, noise from eye blinks, cardiac noise, brain activity signals, etc., each with different frequencies or phase characteristics. As another example, brain activity signals captured by an activity detection sensor 165 may contain not only a combination of alpha, beta, and gamma brain wave signals, but also muscle contraction signals from muscles neighboring the activity detection sensor 165. Activity detection sensors 165 positioned along an upper portion of the liner 225 may have an equal mix of both facial movement signals generated from upper eye muscle contractions of the user and brain activity signals from the frontal lobe of the user.

Inference Module

Figure 4:
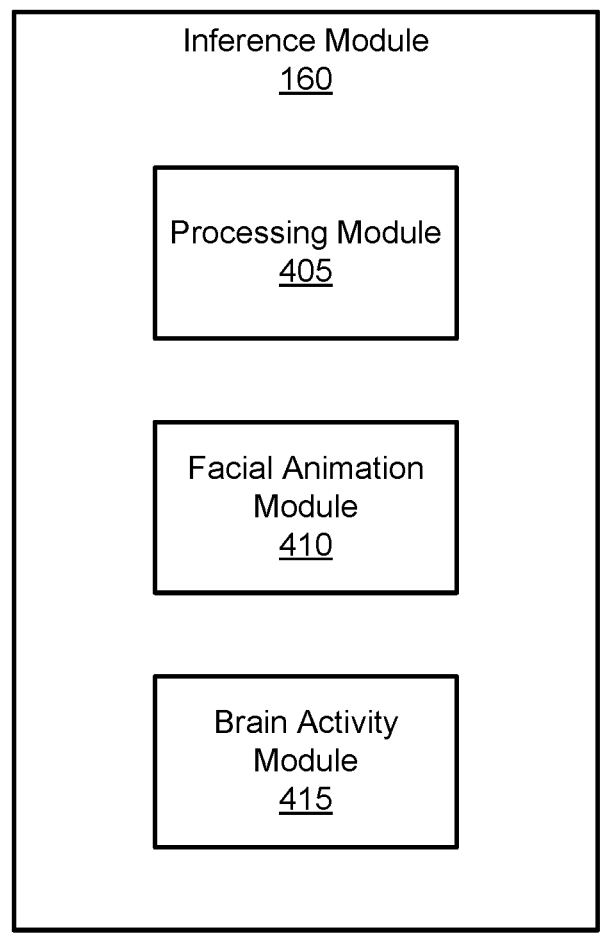
FIG. 4 is a block diagram illustrating the inference module implemented by the virtual reality console, in accordance with an embodiment.

FIG. 4 is a block diagram illustrating the inference module 160 implemented by the virtual reality console 110, in accordance with an embodiment. The inference module 160 includes a processing module 405, a facial animation module 410, and a brain activity module 415. Some embodiments of the inference module 160 have different and/or additional modules than the ones described here. Similarly, the functions can be distributed among the modules in a different manner than is described here. Certain modules and functions can be incorporated into other modules of the inference module 160 and/or other entities on the virtual reality console 110.

The processing module 405 receives and processes signals from the plurality of activity detection sensors 165, and decomposes the received signals to identify a set or combination of individual source signals that constitute the received signals. Each individual source signal may be assumed to have a characteristic amplitude, frequency, phase, etc. Within the set of source signals, the processing module 405 may further identify a set of facial movement source signals that are a subset or a combination of the source signals related to facial movement of the user's upper face. Similarly, within the set of source signals, the processing module 405 may further identify a set of brain activity source signals that are a subset or a combination of the source signals related to the brain activity of the user. The processing module 405 provides the set of source signals to the facial animation module 410 and the brain activity module 415.

The processing module 405 may perform signal processing operations such as low-pass and/or high-pass filtering, noise-reducing operations, averaging, etc. on the received signals. For example, the processing module 405 may apply de-noising filters on the received signals to reduce sensor noise or white noise added to the received signals. As another example, the processing module 405 may identify a set of brain activity source signals by filtering the received signals with characteristic frequencies associated with each of the different brain wave signals.

The processing module 405 may perform blind source separation on the received signals to identify the set of individual source signals that constitute the received signals from the activity detection sensors 165. For example, the processing module 405 may decompose the received signals to identify individual brain activity source signals corresponding to alpha, beta, and gamma brain waves, even though each activity detection sensor 165 detects a combination of these signals. As another example, the processing module 405 may extract individual facial movement source signals corresponding to individual muscles in each position of the activity detection sensors 165, even though each sensor detects a combination of muscle contraction signals from both individual muscles and its neighboring muscles.

In one particular embodiment referred to throughout the remainder of the application, the processing module 160 applies independent component analysis (ICA) to the received signals, in which a signal of an activity detection sensor 165 is assumed to be a linear superposition of multiple independent source signals. It is appreciated, however, that in other embodiments, the processing module 160 alternatively and/or additionally applies other techniques such as principle components analysis (PCA), singular value decomposition (SVD), dependent component analysis (DCA), etc., to perform blind source separation.

The facial animation module 410 receives the set of source signals and projects a facial animation of a user onto the virtual reality environment while the user is wearing or using the VR headset 105. The facial animation module 410 receives the set of source signals from the processing module 405, and translates these signals to a facial animation model of the user for display in the virtual reality environment. In one embodiment, the facial animation model may be a blendshape model that models a user's facial expression by a linear combination of key expression meshes identified for the user.

The brain activity module 415 receives the set of source signals from the processing module 405 and infers the emotional or cognitive state of the user, while the user is using the VR headset 105. For example, the relative intensity of alpha and beta brain waves is indicative of fatigue, relaxation, and concentration of the user. The brain activity module 415 may monitor intensities of different brain waves from the set of source signals and display the cognitive state of the user onto the virtual reality environment, while the VR headset 105 is in use.

SUMMARY

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the invention may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments of the invention may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A head-mounted display device comprising:
    a headset;
    a band attached to the headset, the band configured to fasten the headset in front of an upper portion of a user's face;
    a display panel for displaying a virtual environment, the display panel attached to the headset and positioned in front of the upper portion of the user's face;
    a liner formed around a periphery of the headset, the liner adapted for direct or indirect contact with the upper portion of the user's face; and
    a first plurality of sensors including electrical field sensors that detect electrical signals caused by muscle contractions of the upper portion of the user's face when the user is wearing the head-mounted display device, the first plurality of sensors arranged within an interface between the headset and the user's face along a plurality of locations of the periphery of the headset, such that the first plurality of sensors do not contact the user's face when the user is wearing the head-mounted display device.

2. The head-mounted display device of claim 1, further comprising a second plurality of sensors attached along a plurality of locations of the band that detect electrical signals caused by brain activity of the user when the user is wearing the head-mounted display device.

3. The head-mounted display device of claim 2, wherein the second plurality of sensors are positioned underneath a padding of the band.

4. The head-mounted display device of claim 1, wherein the first plurality of sensors detect electrical signals caused by brain activity of the user when the user is wearing the head-mounted display device, and wherein a portion of the first plurality of sensors are configured to have higher sensitivity to the electrical signals caused by brain activity of the user than the remaining portion of the first plurality of sensors.

5. The head-mounted display device of claim 1, wherein the first plurality of sensors comprise electroencephalogram (EEG) sensors.

6. The head-mounted display device of claim 1, wherein the first plurality of sensors are positioned underneath the liner or underneath a padding of the liner.

7. A method of capturing facial performance of a user with a head-mounted display device, the method comprising:
    collecting electrical signals using a first plurality of sensors including electrical field sensors, wherein the electrical signals are caused by movement of an upper portion of the user's face when the user is wearing the head-mounted display device, and wherein the first plurality of sensors are arranged within an interface between a headset of the head-mounted display device and the user's face along a plurality of locations of a periphery of the headset, such that the first plurality of sensors do not contact the user's face when the user is wearing the head-mounted display device; and
    inputting the electrical signals collected by the first plurality of sensors to a computer software system that drives a display panel of the head-mounted display device for projecting a facial animation model of the user's face to the display panel.

8. The method of claim 7, further comprising:
    collecting electrical signals using a second plurality of sensors attached along a plurality of locations of a band of the head-mounted display device, wherein the electrical signals are caused by brain activity of the user when the user is wearing the head-mounted display device; and
    determining a cognitive state of the user from the electrical signals collected from the first plurality of sensors and the second plurality of sensors.

9. The method of claim 7, wherein the first plurality of sensors comprise electroencephalogram (EEG) sensors.

10. The method of claim 7, wherein the first plurality of sensors are positioned underneath the liner or underneath a padding of the liner.

11. The method of claim 7, wherein the second plurality of sensors are positioned underneath a padding of the band.

12. The method of claim 7, wherein the first plurality of sensors detect electrical signals caused by brain activity of the user when the user is wearing the head-mounted display device, and wherein a portion of the first plurality of sensors are configured to have higher sensitivity to the electrical signals caused by brain activity of the user than the remaining portion of the first plurality of sensors.

* * * * *